United States Patent
Cree

(10) Patent No.: US 8,636,004 B2
(45) Date of Patent: Jan. 28, 2014

(54) CO2 MEASUREMENT IN HIGH RELATIVE HUMIDITY ENVIRONMENTS

(75) Inventor: Robert E. Cree, Newark, NY (US)

(73) Assignee: Dive Cobalt Blue, LLC, Newark, NY (US)

(*) Notice: Subject to any disclaimer, the term of this patent is extended or adjusted under 35 U.S.C. 154(b) by 503 days.

(21) Appl. No.: 13/016,690

(22) Filed: Jan. 28, 2011

(65) Prior Publication Data

US 2012/0192618 A1    Aug. 2, 2012

(51) Int. Cl.
A62B 23/02    (2006.01)

(52) U.S. Cl.
USPC ............. 128/205.12; 128/201.25; 128/205.17

(58) Field of Classification Search
USPC ............ 73/23.3; 128/201.25, 203.12, 203.16, 128/203.17, 204.25, 204.26, 205.12, 128/205.17, 205.27; 436/133
See application file for complete search history.

(56) References Cited

U.S. PATENT DOCUMENTS

| | | | |
|---|---|---|---|
| 2,269,500 A * | 1/1942 | Wildhack | 128/204.25 |
| 4,939,647 A | 7/1990 | Clough et al. | |
| 4,994,117 A | 2/1991 | Fehder | |
| 5,619,987 A * | 4/1997 | Matsuoka | 128/204.29 |
| 5,637,809 A * | 6/1997 | Traina et al. | 73/864.12 |
| 5,924,418 A | 7/1999 | Lewis | |
| 6,003,513 A | 12/1999 | Readey et al. | |
| 6,200,819 B1 * | 3/2001 | Harvey et al. | 436/179 |
| 6,408,847 B1 | 6/2002 | Nuckols et al. | |
| 6,526,971 B2 | 3/2003 | Kellon | |
| 6,712,071 B1 | 3/2004 | Parker | |

(Continued)

FOREIGN PATENT DOCUMENTS

WO    99/03524    1/1999

OTHER PUBLICATIONS

Mitchell, Dr. Simon: Analysing Carbon Dioxide with Dr. Simon Mitchell website with video (http://www.submergeproductions.com/videos.aspx?mode+episodeview& channelid+3&episodeid+107), pp. 1-2, Nov. 11, 2010.

(Continued)

*Primary Examiner* — Lisa Caputo
*Assistant Examiner* — Punam Roy
(74) *Attorney, Agent, or Firm* — Brian B. Shaw, Esq.; Harter Secrest & Emery LLP

(57) ABSTRACT

A CO2 measuring device for use in a high humidity environment typically found in re-breathing apparatus, especially underwater re-breathing apparatus, that allows commonly available CO2 gas detectors to function properly and further provides for remote, continuous and/or quantitative sensing of CO2. Under normal conditions found inside re-breathers, a 100% relative humidity condensing environment exists that prevents the use of commercially available CO2 detectors which typically require relative humidity to be less than about 90 to 95% for proper operation. A venturi mixing device is disclosed that is driven by pressurized makeup gases routinely added into the re-breathing loop, acting to draw and mix with a portion of the moisture laden gas from the re-breather environment, creating a combined gas mixture with relative humidity well within the operating range of commercially available CO2 detectors. CO2 measurements can advantageously be corrected by the venturi mixing proportions to gain a quantitative analysis of CO2 levels present in the pre-sampled 100% relative humidity condensing environment. The excess drive energy provided by the pressurized makeup gas allows for longer sampling lines that can be advantageously placed adjacent to the mouth of the re-breathing individual allowing CO2 measurement from a remote location and when drive gas is constantly applied, further allowing for continuous measurement of CO2.

14 Claims, 1 Drawing Sheet

(56) References Cited

U.S. PATENT DOCUMENTS

| | | | |
|---|---|---|---|
| 7,389,703 B2* | 6/2008 | Wei et al. | 73/863.03 |
| 7,520,280 B2* | 4/2009 | Gordon | 128/205.28 |
| 2001/0015203 A1 | 8/2001 | Cumming | |
| 2008/0135044 A1* | 6/2008 | Freitag et al. | 128/200.26 |
| 2010/0012124 A1 | 1/2010 | Deas | |

OTHER PUBLICATIONS

GSS (Gas Sensing Solutions) C20 Data sheet for a typical CO2 detector—lists 0-95% RH spec (6 pages), Jan. 29, 2010.

U.S. Appl. No. 13/016,673, filed with the USPTO on Jan. 28, 2011 (26 pages).

U.S. Appl. No. 13/016,664, filed with the USPTO on Jan. 28, 2011 (34 pages).

* cited by examiner

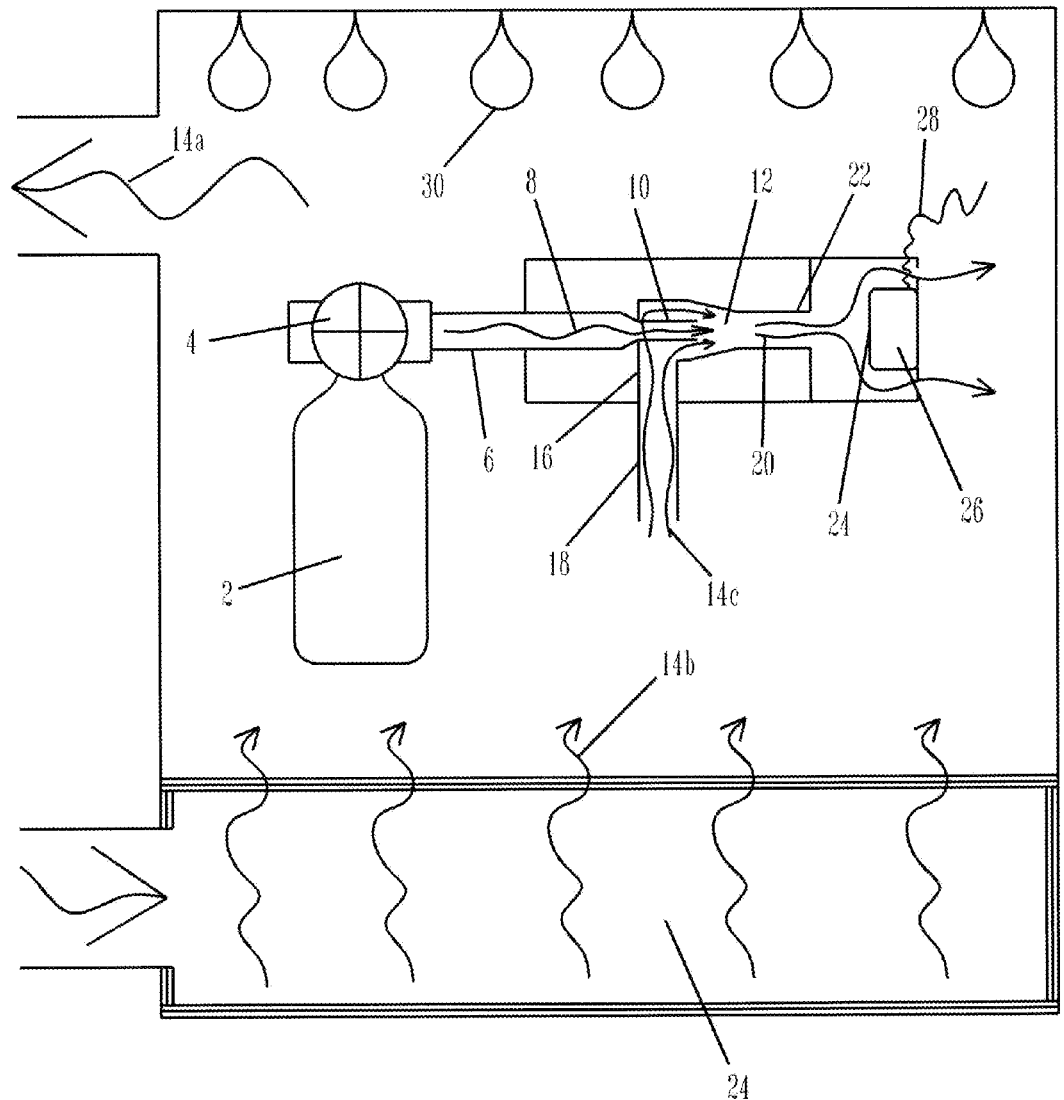

CO2 MEASUREMENT IN HIGH RELATIVE HUMIDITY ENVIRONMENTS

CROSS-REFERENCE TO RELATED APPLICATIONS

Not applicable.

STATEMENT REGARDING FEDERALLY SPONSORED RESEARCH OR DEVELOPMENT

Not applicable.

REFERENCE TO A "SEQUENCE LISTING"

Not applicable.

FIELD OF THE INVENTION

The present system provides for CO2 measurement in a re-breathing apparatus with breathing gas conditioned to allow for more reliable detection of CO2 and with the possibility to sample from a remote location within the re-breathing apparatus.

BACKGROUND OF THE INVENTION

For individuals venturing into underwater environments, breathable gas is typically delivered from a compressed gas storage tank and demand system known as SCUBA (Self Contained Underwater Breathing Apparatus). The most common form termed open circuit, releases pressurized gas through a regulator which contains a diaphragm located adjacent the diver's mouth that senses and is responsive to the divers breathing pressure. The diaphragm acts to move a demand valve to deliver breathing gas to the diver when required and all subsequently exhaled gas typically passes back into the regulator and is directed through a one way valve into the surrounding environment where it is permanently lost for use by the diver. During inhalation, the one way valve seals the regulator off from the surrounding environment to prevent water from back flowing and choking the diver. The sensitivity of present art regulators is such that very little effort is required to inhale or exhale underwater. Since open circuit gas is used only once, divers are required to carry a large volume of pressurized gas proportional to the inhalation rate of the diver as well as to the depth the gas is breathed, which limits the amount of time a diver has available underwater to the amount of gas carried with them. As depths increase, ambient pressure increases by about 1 atmosphere for every 33 feet/10 meters. At a depth of 33 feet/10 meters, the diver is subjected to 2 atmospheres of pressure (one atmosphere at the surface plus one additional for the 33 feet/10 meters of water) and a scuba tank will last only ½ as long as it would at the surface, and at depths of 300 feet now commonly visited by divers, that same tank will last about 1/10 the duration at the surface.

As time underwater and depth continue to increase, divers increase the size and quantity of tanks until the bulk and complexity are too much to handle. To deal with this issue, divers are turning to devices known as re-breathers that capture exhaled gas in one or more flexible storage container, known commonly as a counterlung, and return a portion to the diver for re-breathing. By recycling the breathed gas, re-breathers extend usable time from a given amount of gas, by as much as 20 times. To recycle exhaled gas, the re-breather must eliminate unwanted carbon dioxide (CO2) naturally introduced by the body as part of the respiration process or death can result. To do this, re-breathers process breathing gas in a loop like fashion to pass through a device known as a CO2 scrubber containing a suitable chemical agent such as lime that chemically absorbs CO2, releasing heat and water in a well understood process. As long as the scrubber is appropriately sized and designed, CO2 free gas results that is then returned back to the diver to be breathed again, forming what is known in totality as a breathing loop.

In all presently implemented systems, re-breathed gas is driven through the loop directly by the breathing pressure of the diver and present art re-breathers require more breathing effort compared to open circuit, thus it is very important to minimize flow restrictions in the breathing loop to maintain the work of breathing (WOB) to reasonable levels. The duration and CO2 removal capability of the scrubber is increased by employing larger, more complex scrubbers filled with agent made with finer sized granules that all act together to increase the total available active surface area, and unfortunately, also act to increase the WOB required in the loop. Work of breathing and scrubber duration are two of the most important performance criteria for re-breathers since it is critical to the survival of the diver that they be able to breathe easily enough to adequately ventilate the body with enough metabolic oxygen to survive as well as expel CO2 that is metabolically produced by the body. Once outside the body, CO2 must be continually and effectively removed from the breathing loop by the scrubber or an incapacitating condition known as hypercapnia can result which, although it might be survivable at the surface, can easily lead to death while underwater. It is particularly desirable to reduce the WOB of the entire rebreathing system and add safety features that would otherwise not be practical due to the associated increase in WOB such as an improved CO2 scrubber.

One idea to reduce WOB that several divers have considered and typically rejected for reasons of complexity, uses compressed gas carried by the diver to assist the counterlung in expansion and contraction during breathing such as described in U.S. published patent application No. 2001/0015203. This approach, teaches about a device that adds pressurized drive gas to a small isolated sub-section of the flexible storage container that collects exhaled breathing gas from the diver, where the added drive gas acts to assist the diver in the exhalation process. Inhalation is also assisted by bleeding off the added pressurized drive gas to allow the flexible storage container to forcibly contract. The device trades work by the diver for work by the drive gas acting on the flexible storage container to move breathing gas through the loop resulting in a reduction in WOB by the diver. The extra motive force created by the drive gas acting on the flexible storage container also creates higher pressures in the breathing loop rather than in the diver's lungs. With each breathe, the volume of added drive gas builds up and must be vented from the loop or an over pressurize condition will result. The device features one way pressure relief valves to rid the breathing loop of this excess breathing gas and exhaust it to the surrounding environment. Ideally, this exhaust would occur once the flexible storage container is fully expanded and cannot contain additional gas. In this case assisted breathing no longer will function and the diver must create the motive force to expel the excess gas. Accordingly, these one way valves must be set to open at a pressure low enough that allows the diver to comfortably expel excess breathing gas without assistance when the loop is filled to full capacity. Unfortunately, the higher loop pressures that occur during assisted breathing causes breathing gas to undesirably escape from the loop through the one way pressure relief valves set to relieve at these lower pressures and extensive testing has shown that so much breathing gas is lost as to render the concept useless. It would be extremely desirable to provide an assisted re-breathing device that does not prematurely leak breathing gas to the surrounding environment during assisted breathing which also provides for unassisted exhalation of excess breathing gas from the loop to the surrounding environment by the diver with a lower breathing pressure similar to open circuit scuba.

In prior art re-breathers, additional one way valves are used to ensure un-scrubbed exhale gas laden with CO2 is not re-breathed and is instead directed to pass properly through the scrubber. These valves are typically located as close to the mouth as possible to minimize the volume of gas that can be directly re-inhaled, one positioned to allow exhaled gas to pass down into the re-breather for temporary storage and scrubbing and a separate one turned in the opposite direction to receive scrubbed gas back from the re-breather and pass it back to the diver for inhalation. Most one way valves are designed as simple flexible membranes that under reverse flow conditions, normally act to effectively seal off flow passages and open only under forward flow conditions to allow flow to move in the proper direction around the loop. These one way valves resist the flow of breathing gas and add to the WOB, increasing resistance with increased breathing gas flow. To reduce WOB, a minimum number of one way valves are used and their size is maximized. Many accidents have been reported involving the failure of one way valves that allowed exhaled gas to be directly re-inhaled, leading to buildup of CO2 in the loop. It is highly desired to maintain loop flow direction integrity when failure of a one way check valve occurs.

Particularly insidious is that hypercapnia can arise quite rapidly. A condition commonly known as breakthrough occurs when the scrubbing agent is depleted in any location enough to allow a significant portion of CO2 to pass through the scrubber, rendering it unusable. It is well understood that heavy breathing and/or deeper depths cause CO2 to pass further through the scrubber which can lead to early breakthrough. Breakthrough can also occur due to improper packing of the agent into the scrubber with a condition known as channeling, where re-breathed gas follows a low resistance to gas flow path that quickly depletes the locally surrounding scrubbing agent and allows CO2 to prematurely channel through the scrubbing bed. Warning systems for the presence of CO2 have only recently been introduced with limited success due to extreme sensitivity exhibited by available sensors to high relative humidity environments such as what exists naturally in a re-breather loop. Prior art systems that do exist, employ barriers made of sponges and/or water impermeable membranes placed between the loop and the sensor to limit water intrusion, which unfortunately also degrades the response time of the sensor, making it relatively ineffective when CO2 rapidly builds up, or worse, can render the sensor useless if water saturation of the barrier occurs. Instead, most divers today rely on indirect measurements such as the time a scrubbing agent bed has been in service versus conservative experience as well as the direct measurement of scrubber temperature to determine when to stop using the bed. Since the scrubbing process naturally generates heat, a temperature rise indicates the agent is being activated by the presence of CO2 and when this occurs near the end of the bed, it is time to stop using the re-breather. Unfortunately, CO2 breakthrough tends to occur quite suddenly, especially during periods of heavy exertion and/or at deeper depths, making predictions based on time and temperature quite fallible. Due to significant safety concerns, re-breather divers would like to quickly and reliably monitor for the life threatening presence of CO2 in the loop, especially at higher work levels and/or deeper depths when a rapid buildup can occur without warning.

Re-breathers also must provide make up for oxygen absorbed from inhaled gas by the body to satisfy the metabolic needs of the diver. It is well understood that at constant workload, the rate of metabolic oxygen consumption is more or less constant, requiring roughly the same number of O2 molecules per unit time, meaning oxygen consumption is proportional to mass flow. Additionally, it is well known that metabolism and associated oxygen consumption by the divers body, changes more or less proportional to workload and respiration rate, therefore the harder you work, the higher the respiration rate, and the larger the mass flow requirement for metabolic makeup oxygen. Similar to open circuit gas consumed with depth, if a fixed mass sample of oxygen were isolated in a flexible container at the surface, it would shrink to ½ the volume at 33 feet and 1/10th the volume at 300 feet, yet this fixed mass would sustain the diver for the same period of time metabolically. Overall, metabolic consumption requires makeup oxygen volumetric flow to increase proportional to respiration rate and drop inversely proportional to depth induced pressure.

In diving operations, the amount of oxygen present in the breathing gas is measured in terms of oxygen partial pressure or PO2, usually expressed in standard atmospheres of pressure. Normal oxygen at the surface is 21% of one atmosphere and is expressed as 0.21 PO2, whereas 100% pure oxygen at the surface is 1.00 PO2. It is well recognized that for safe diving operations, the oxygen content of breathing gas should always remain in the range of about 0.16<PO2<1.60. Too little oxygen, known as hypoxia, is a deadly condition that occurs below around 0.16 PO2, where insufficient oxygen is present to sustain life. Too much oxygen, termed hyperoxia, becomes toxic over time to the central nervous system (CNS). Commonly referred to by divers as CNS toxicity, high oxygen levels eventually lead to uncontrolled convulsions, which when convulsions occur underwater, place the diver at extreme risk of death due to drowning. Typically this condition strikes without warning, and evidence supports that toxicity is accelerated by elevated CO2 levels. Several prior art methods are used in re-breathers, that attempt to maintain safe levels of oxygen in the breathing loop.

One method, such as employed in U.S. Pat. No. 6,526,971 and present art rebreathers known as the RB80, forcibly eject a portion of the exhaled gas from the loop that is replaced by passive addition of a gas mix containing some amount of oxygen, linked to the respiration rate of the diver. Oxygen levels in the loop drop and stabilize to several percent below injected levels. Divers must be very careful not to allow hypoxia to set in, especially at shallower depths where the percent drop is amplified. Another method allows the diver to manually actuate a valve to add oxygen to the loop as required. Yet another method bleeds oxygen into the loop using a fixed orifice driven by a special regulator designed to maintain a constant, absolute pressure on one side of the orifice, with ambient pressure on the other, with enough differential pressure to cause sonic flow through the orifice. As ambient pressure increases with depth, pressure across the orifice drops, producing a roughly constant mass flow of oxygen as depth changes in a well understood process that is not linked to the respiration rate of the diver. As ambient pressure increases sufficiently to cause the orifice to drop into sub-sonic operation, mass flow is reduced, ultimately to zero when ambient pressure equals the set pressure of the absolute pressure regulator. In these systems, the diver normally chooses an orifice sized to produce flow somewhat below their resting metabolic rate such that an occasional manual add of oxygen is required to make up for any shortfall and more frequent additions are required at deeper depths when the orifice goes sub-sonic and with increased workloads. It is very important in these systems that the diver closely monitor oxygen content within the breathing loop so that timely additions can be made to remain safe. Another system automatically monitors and controls oxygen addition using an electronic closed loop computer control system that periodically cycles an electric oxygen addition valve to maintain oxygen levels within the loop. Electronic systems are susceptible to failure in underwater environments and it is very important that oxygen monitoring sensors be accurate to facilitate safe operation of re-breathers employing them.

Prior art oxygen monitoring within the re-breathing loop is commonly accomplished using some form of galvanic sensor which unfortunately, are proven in practice to not be all that reliable. Sensors typically exhibit a relatively short life expectancy of just several months to a year or two, are also susceptible to malfunction when exposed to condensing water and provide little warning they are about to fail. When they do wear out or fail, they report oxygen levels different from what is actually present. Due to reliability concerns, divers typically employ multiple sensors, sequence them in age, and even employ sophisticated real time computer algorithms to determine the health and believability of sensors. In the end, sensor health is left up to the diver to evaluate and this requires constant vigilance to remain safe. It is particularly desirable to eliminate the need for electronic controls and sensor feedback to properly add and maintain oxygen levels in underwater re-breathing devices.

BRIEF SUMMARY OF THE INVENTION

A device is provided for reducing the relative humidity of a high humidity gas environment to levels which allow commonly available CO2 gas detectors to function properly and is particularly suitable for use in re-breathing apparatus where a 100% relative humidity condensing environment exists, and especially in an underwater re-breathing apparatus. According to manufacturer specifications and in practice, these CO2 detectors typically require relative humidity to be less than about 90 to 95% to properly operate. A venturi mixing device is disclosed, driven by relatively dry pressurized makeup gases routinely added into the re-breathing loop during normal operation, that draws a portion of the moisture laden gas from the re-breather environment into the venturi where the two gases mix to create a combined gas mixture with relative humidity well within the operating range of present CO2 detectors.

Further, CO2 measurements can be corrected for the venturi mixing proportions to gain a quantitative analysis of CO2 levels present in the pre-sampled 100% relative humidity condensing environment.

Additionally, the excess drive energy provided by the pressurized makeup gas, allows for longer sampling lines to be used that can be advantageously placed adjacent to the mouth of the re-breathing individual allowing CO2 measurement from a remote location and when drive gas is constantly applied, further allowing for continuous measurement of CO2.

Other features and advantages will become apparent from the following detailed description, the drawings, and the claims.

BRIEF DESCRIPTION OF THE SEVERAL VIEWS OF THE DRAWING

FIG. 1 is a schematic, cross section view of a venturi CO2 detection device suitable for use in one hundred percent relative humidity, condensing, gas environments

DETAILED DESCRIPTION OF THE INVENTION

Referring to FIG. 1, this preferred embodiment depicts a commonly available venturi arrangement made up of venturi nozzle 10, venturi suction port 16, and venturi mixing chamber 12. High pressure gas storage bottle 2 with attached high pressure regulator 4, delivers pressurized dry CO2 free gas 8 either in pulses or continuously through connecting port 6 to the pressure input of the venturi, feeding pressurized dry CO2 free gas 8 into venturi nozzle 10. Pressurized dry CO2 free gas 8 exits venturi nozzle 10 into venturi mixing chamber 12 where it creates a low pressure suction according to well understood principles, and acts to draw high humidity sample gas 14c through sample tube 18 into venturi suction port 16 where it mixes with pressurized dry CO2 free gas 8 in venturi mixing chamber 12 to form a lower relative humidity gas mixture 20 which exhibits a relative humidity substantially lower than 95% non-condensing which is suitable for sensing by common commercially available CO2 sensing devices.

In diving re-breathing applications, breathing gas 14a travels in a loop like fashion through the divers body and around what is commonly known as a re-breathing loop which includes CO2 removal device 24 where it picks up humidity in a well understood process until it is typically reaches 100% relative humidity with condensation 30 typically being present. High humidity CO2 scrubbed re-breathing gas 14b exits CO2 removal device 24 and travels into the area of sample tube 18 where a small portion of it is drawn through sample tube 18 and into venturi suction port 16 as high humidity sample gas 14c to determine if any CO2 is present in high humidity CO2 scrubbed re-breathing gas 14b, indicating the failure of CO2 removal device 24, which is life threatening to the diver. In diving operations, high pressure storage bottle 2 will normally contain breathing gas that has been dried according to industry standards and enters through connecting port 6 at much less than 1% relative humidity. Commonly available venturi systems will typically draw one part from venturi suction port 16 for every one half to three parts passed through venturi nozzle 10. This provides a lower relative humidity gas mixture 20 which falls typically between, but is not limited to 33% relative humidity up to 75% relative humidity, non-condensing, which is well below the maximum specification for common commercially available CO2 sensors. For commonly available CO2 sensors to properly function, the venturi system must draw at least one part from venturi suction port 16 for every 10 to 20 parts passed through venturi nozzle 10 so that the relative humidity of lower relative humidity gas mixture 20 falls to the required 90 to 95% range respectively.

Lower relative humidity gas mixture 20 passes out of venturi exit 22 and flows around CO2 sensor face 24. CO2 sensor 26 detects the presence of CO2 in lower relative humidity gas mixture 20 and provides an electrical signal proportional to the amount of CO2 present in lower relative humidity gas mixture 20 through CO2 sensing wires 28 for subsequent analysis and use by the diver. It is not critical that a precise determination be made of exact CO2 content to warn of the failure of CO2 removal device 24, only that CO2 is either present or not present. A venturi mixing correction factor, determined from manufacturer specifications for the chosen venturi and typically in the range of, but not limited to, 1.3 up to 3, can be multiplicatively applied to CO2 levels detected in lower relative humidity gas mixture 20, to obtain a quantitative CO2 measurement contained in high humidity sample gas 14c.

When pressurized dry CO2 free gas 8 is delivered in pulses, pulses can advantageously be generated using existing pulsed makeup gases such as described in concurrently filed co-pending application Ser. No. 13/016,664, now published as US 2012/0192868 A1, by the same inventor as the present application, entitled GAS ASSISTED RE-BREATHING DEVICE and hereby incorporated by reference. Here pressurized dry CO2 free gas 8 is delivered as pulsed oxygen rich gas intended for metabolic oxygen makeup for the re-breathing individual.

Sample tube 18 can be of any length suitable to the available drive energy provided by pressurized drive gas 8 which allows the possibility to locate the bulk of the CO2 measuring device remote from the sample point. Sample tube 18 can be advantageously positioned to draw high humidity sample gas 14c from a remote location adjacent to the mouth of the re-breathing individual where little room is typically available. Additionally, when pressurized drive gas 8 is continuously applied through connecting port 6 to venturi nozzle 10, continuous measurement of CO2 is possible. When continuously sampling adjacent to the mouth, both inhaled and exhaled CO2 measurements can advantageously be made which provides a direct measurement of metabolic CO2 released by the re-breathing individual, such as is well known in medical applications, as well as indicating a failure of CO2 removal device 24.

The invention has been described in detail with particular reference to a presently preferred embodiment, but it will be understood that variations and modifications can be effected within the spirit and scope of the invention. The presently disclosed embodiments are therefore considered in all respects to be illustrative and not restrictive. The scope of the invention is indicated by the appended claims, and all changes that come within the meaning and range of equivalents thereof are intended to be embraced therein.

The invention claimed is:

1. A method of providing a gas mixture to a CO2 measurement device in a re-breather, the method comprising:
    (a) passing a relatively dry gas having a known CO2 level through a venturi to entrain a higher humidity gas to form a gas mixture within operating parameters of the CO2 measurement device; and
    (b) exposing the gas mixture to the CO2 measurement device.

2. The method of claim 1, wherein the known CO2 level is substantially 0.

3. The method of claim 1, further comprising determining a performance of the re-breather in response to the gas mixture exposed to the CO2 measurement device, independent of a proportion of the relatively dry gas and the higher humidity gas in the gas mixture.

4. The method of claim 1, further comprising detecting a presence of CO2 in the relatively dry gas and applying a venturi mixing correction factor to obtain a quantitative CO2 measurement of the higher humidity gas.

5. The method of claim 1, further comprising performing steps (a) and (b) in an underwater environment.

6. The method of claim 1, further comprising employing a substantially CO2 free oxygen rich gas as the relatively dry gas, the CO2 free oxygen rich gas sufficient to provide metabolic oxygen in the re-breather.

7. The method of claim 1, further comprising substantially continuously passing the relatively dry gas through the venturi.

8. The method of claim 1, further comprising drawing the higher humidity gas through a sample tube from a remote location before entering the venturi.

9. A high relative humidity environment CO2 measurement device for use in a re-breather having a breathing loop, the device comprising:
    (a) a venturi fluidly connected to the breather loop, the venturi having an outlet and a motive inlet;
    (b) a source of pressurized relatively dry gas of a known CO2 level fluidly connected to the motive inlet; and
    (c) a CO2 sensor operably connected to the outlet;
        wherein the pressurized relatively dry gas passes through the venturi and draws in and mixes with gas from the breathing loop to form gas mixture passing from the outlet of the venturi to the CO2 sensor.

10. The device of claim 9, wherein the presence of CO2 is detected in the gas mixture independent of a mixing proportion of the venturi.

11. The device of claim 9, wherein a venturi mixing correction factor is applied to an output of the CO2 sensor to obtain a quantitative CO2 measurement.

12. The device of claim 9, wherein the CO2 sensor is selected to operate at underwater pressures.

13. The device of claim 9, wherein the pressurized relatively dry gas is continuously passed through the venturi.

14. The device of claim 9, further comprising a sample tube extending from the venturi, wherein the gas from the breathing loop passes through the sample tube to the venturi.

* * * * *